US011857750B2

(12) United States Patent
Razavi et al.

(10) Patent No.: US 11,857,750 B2
(45) Date of Patent: Jan. 2, 2024

(54) VASCULAR ACCESS SYSTEMS AND METHODS

(71) Applicants: Mahmood Razavi, Orange, CA (US); Bhavraj Khalsa, Orange, CA (US); Meena Michael Archie, Orange, CA (US)

(72) Inventors: Mahmood Razavi, Orange, CA (US); Bhavraj Khalsa, Orange, CA (US); Meena Michael Archie, Orange, CA (US)

(*) Notice: Subject to any disclaimer, the term of this patent is extended or adjusted under 35 U.S.C. 154(b) by 139 days.

(21) Appl. No.: 17/472,378

(22) Filed: Sep. 10, 2021

(65) Prior Publication Data
US 2022/0080176 A1 Mar. 17, 2022

Related U.S. Application Data

(60) Provisional application No. 63/135,376, filed on Jan. 8, 2021, provisional application No. 63/078,246, filed on Sep. 14, 2020.

(51) Int. Cl.
*A61M 39/02* (2006.01)

(52) U.S. Cl.
CPC ... *A61M 39/0247* (2013.01); *A61M 2039/027* (2013.01); *A61M 2039/0258* (2013.01); *A61M 2205/0266* (2013.01)

(58) Field of Classification Search
CPC ...... A61M 39/0247; A61M 2039/0258; A61M 2039/027
See application file for complete search history.

(56) References Cited

U.S. PATENT DOCUMENTS

| | | | | |
|---|---|---|---|---|
| 4,318,401 A | * | 3/1982 | Zimmerman | ..... A61M 39/0247 604/165.01 |
| 6,544,206 B1 | | 4/2003 | Johnston, Jr. | |
| 7,118,546 B2 | * | 10/2006 | Blatter | ................ A61M 1/3661 604/4.01 |
| 8,591,538 B2 | | 11/2013 | Gellman | |
| 8,679,053 B2 | | 3/2014 | von Segesser | |
| 9,078,982 B2 | | 7/2015 | Lane et al. | |

(Continued)

FOREIGN PATENT DOCUMENTS

| WO | WO 2015/052235 | 4/2015 |
|---|---|---|
| WO | WO 2020/074856 | 4/2020 |

OTHER PUBLICATIONS

International Search Report for Application No. PCT/US2021/049955 dated Nov. 25, 2021 in 9 pages.

*Primary Examiner* — Dung T Ulsh
(74) *Attorney, Agent, or Firm* — Knobbe, Martens, Olson & Bear, LLP

(57) ABSTRACT

A vascular access system can include a port configured to be implanted outside of a target body lumen, at least one conduit fluidly connected to the port, and at least one one-way valve proximate the distal end of the conduit and within the fluid pathway of the sidewall of the conduit. The system can also include a gateway element comprising a through lumen operably connected to an outer diameter of the conduit, the gateway element comprising a first radially compressed configuration in which the gateway element causes occlusion within the through lumen, and a second radially expanded configuration in which the gateway element permits passage of fluids within the through lumen.

29 Claims, 6 Drawing Sheets

(56) References Cited

U.S. PATENT DOCUMENTS

| | | | |
|---|---|---|---|
| 2013/0253279 A1* | 9/2013 | Smith | A61M 39/0247 |
| | | | 600/204 |
| 2016/0089181 A1* | 3/2016 | Johnson | A61B 1/00087 |
| | | | 600/104 |
| 2016/0361529 A1* | 12/2016 | Finch, Jr. | A61M 1/3659 |
| 2017/0014612 A1* | 1/2017 | Lundgren | A61M 5/14 |
| 2017/0095644 A1* | 4/2017 | Stephan | A61M 39/0247 |
| 2018/0221593 A1 | 8/2018 | Peh et al. | |
| 2018/0221994 A1 | 8/2018 | Eckhard et al. | |
| 2018/0243004 A1 | 8/2018 | von Segesser | |
| 2020/0038228 A1* | 2/2020 | Aravalli | A61F 5/449 |
| 2020/0114060 A1* | 4/2020 | Vartanian | A61M 1/3655 |

\* cited by examiner

VASCULAR ACCESS SYSTEMS AND METHODS

CROSS-REFERENCE TO RELATED APPLICATIONS

This application claims priority benefit to U.S. Provisional Patent Application No. 63/078,246, filed Sep. 14, 2020 and U.S. Provisional Patent Application No. 63/135,376, filed Jan. 8, 2021, the entirety of each is hereby incorporated by reference herein.

BACKGROUND

End-stage renal disease (ESRD) affects nearly 500,000 patients in the United States, and that number is unfortunately growing due to common comorbidities including diabetes, hypertension, hyperlipidemia, atherosclerosis, and others. As a result, the global dialysis market is projected to grow from an estimated $74.2 billion in 2019 to $99.2 billion by 2024 at a CAGR of 6.0%. Currently, ESRD patients undergo long term dialysis by one of three main access routes: a peritoneal dialysis catheter, an arteriovenous graft/fistula, or a tunneled dialysis catheter. Each of these come with their own risks, but the greatest issue is the need for repeat visits to the hospital or surgery centers for maintenance and repair of malfunctioning dialysis access, including but not limited to thrombosis, stenosis, bleeding, aneurysm, and infection. Improved, more durable dialysis access systems and methods are needed.

SUMMARY

Some embodiments of the invention create improved mechanisms for luminal access of a body. Luminal access can be, for example, vascular access, including but not limited to dialysis access, as well as access for delivery of one, two, or more therapeutic agents into the vascular system, such as chemotherapeutic agents, antimicrobial agents, and others. Vascular access can be, for example, into an artery or vein. Luminal access can be configured for non-vascular access in other embodiments.

Systems and methods as described herein can be placed by both percutaneous and open surgical methods. Several advantages of embodiments of the invention include the ability to limit access failure, infection, and need for end-stage renal disease (ESRD) patient visits to the hospital.

Some embodiments advantageously shift the current paradigm of first placing a tunneled catheter, then creating an arteriovenous fistula or graft. Some embodiments aim to provide long term vascular access, including but not limited to dialysis access with the placement of "access windows" that may be percutaneously or surgically placed, and create high-quality, durable devices for dialysis access. Some embodiments can lead to any number of the following advantages: (1) lower profile access system; (2) reduces catheter thrombosis (clot inside the catheter); (3) reduces vascular site thrombosis (clotting of the point of access); (4) reduces vascular route thrombosis (clotting the vessels the catheters resides in or passes through); (5) reduces fibrosis/scarring/stenosis of the lumens it is intended to reside in or pass through (e.g., due to a much smaller diameter/footprint in a target lumen when not in use); and (6) potential reduction in infection rate.

Some embodiments can comprise, consist essentially of, consist of, and/or not comprise any number of the features in the disclosure, including but not limited to:

a port allowing access, e.g., external such as configured for access to a body of a patient;

the port may be entirely subcutaneous, partially exposed or fully exposed;

allow for repeated accesses;

connected to a subcutaneous element that provides intravascular access;

subcutaneous element may be catheter tubing or flexible shape memory material, metallic, plastic, or other blended materials such as nitinol and/or silicone;

subcutaneous element may comprise single channel/lumen or multiple channels/lumens;

port and subcutaneous element allow for flow of blood or other fluids into and out of the body port and subcutaneous element allow for entry of wires, catheters, or other medical devices including, but not limited to balloons and stents;

port may be separated and reattached to subcutaneous element before or after implantation;

subcutaneous element may be separated, removed, or exchanged for a new subcutaneous element when desired, e.g., in the event of malfunction;

subcutaneous element may be removed and exchanged over wire or inserted de novo;

subcutaneous element and intravascular portion allows for expansion, either by introduction of larger catheters/sheaths/devices within the element or via an external control element/knob incorporated into the port hub.

In some embodiments, disclosed herein is a luminal access system, such as a vascular or non-vascular access system, comprising any number of: a port configured to be implanted outside of a target body lumen; at least one conduit fluidly connected to the port, the conduit comprising an open proximal end, an open distal end; and a sidewall defining a fluid pathway therethrough; at least one one-way valve proximate the distal end of the conduit and within the fluid pathway of the sidewall of the conduit; and/or a gateway element comprising a through lumen operably connected to an outer diameter of the conduit, the gateway element comprising a first radially compressed configuration in which the gateway element causes occlusion within the through lumen, and a second radially expanded configuration in which the gateway element permits passage of fluids within the through lumen.

In some embodiments, the gateway element comprises a shape memory material.

In some embodiments, the shape memory material comprises nitinol.

In some embodiments, the port is configured to be detachable from the conduit.

In some embodiments, the conduit comprises a plurality of fluid pathways.

In some embodiments, the gateway element comprises a cylindrical portion.

In some embodiments, the diameter of the second radially expanded configuration is at least about 50% greater than the first compressed configuration.

In some embodiments, the diameter of the second radially expanded configuration is at least about 100% greater than the first compressed configuration.

In some embodiments, a diameter of the conduit is between about 4 mm and about 6 mm.

In some embodiments, a total axial length of the conduit is between about 3 cm and about 9 cm.

In some embodiments, the port is configured to be at least partially subcutaneously implanted.

In some embodiments, the port comprises a removable cap configured to reside above the skin surface.

In some embodiments, the system also includes a plurality of conduits, each conduit comprising a plurality of one-way valves.

In some embodiments, disclosed herein is a method of providing access to a target blood vessel, comprising: implanting a port subcutaneously or above the skin and outside of a target blood vessel; positioning a conduit such that a proximal end of the conduit is fluidly connected to the port and a distal end of the conduit is positioned within the target blood vessel, the conduit comprising at least one one-way valve within the conduit and proximate the distal end of the conduit; and/or expanding a gateway element connected proximate the distal end of the conduit such that a first component of the gateway element is positioned outside a sidewall of the target blood vessel, a second component of the gateway element is positioned inside the sidewall of the target blood vessel, and less than about 5 mm of the distal end of the conduit is positioned within the target blood vessel.

In some embodiments, the gateway element comprises a shape memory material.

In some embodiments, disclosed herein is a method of providing access to a target blood vessel, comprising any number of: radially expanding a gateway element extending within a subcutaneous tract of a patient, the gateway element comprising a distal end positioned within a target blood vessel; accessing a port outside of the target blood vessel; advancing a medical device through the port, into a conduit within the gateway element, through at least one-way valve, and into the target blood vessel.

In some embodiments, the gateway element comprises a shape memory material, and a first component of the gateway element is positioned outside a sidewall of the target blood vessel, a second component of the gateway element is positioned inside the sidewall of the target blood vessel.

In some embodiments, the method further comprises withdrawing fluid from the target blood vessel through the medical device.

In some embodiments, the method further comprises infusing a therapeutic agent from the target blood vessel through the medical device.

In some embodiments, the method further comprises performing hemodialysis via the medical device.

In some embodiments, the target blood vessel comprises a vein.

In some embodiments, the method comprises a plurality of conduits, each conduit comprising a plurality of one-way valves.

In some embodiments, radially expanding the gateway element comprises passively radially expanding the gateway element.

In some embodiments, radially expanding the gateway element comprises actively radially expanding the gateway element.

In some embodiments, actively radially expanding the gateway element comprises actuating a control to radially expand the gateway element.

In some embodiments, the method further comprises radially contracting the gateway element to minimize dead space and promote occlusion within the gateway element.

In some embodiments, radially contracting the gateway element occurs following withdrawing the medical device from the patient.

In some embodiments, disclosed herein is a luminal access system, comprising any one or more of the embodiments described in the disclosure.

In some embodiments, disclosed herein is a luminal access method, comprising any one or more of the embodiments described in the disclosure.

In some embodiments, a vascular access system is provided. The vascular access system can include a port configured to be implanted outside of a target body lumen. The vascular access system can include at least one conduit fluidly connected to the port. In some embodiments, the conduit comprises an open proximal end, an open distal end, and a sidewall defining a fluid pathway therethrough. The vascular access system can include at least one one-way valve proximate the distal end of the conduit and within the fluid pathway of the sidewall of the conduit. The vascular access system can include a gateway element comprising a through lumen operably connected to an outer diameter of the conduit. In some embodiments, the gateway element comprises a first radially compressed configuration in which the gateway element causes occlusion within the through lumen, and a second radially expanded configuration in which the gateway element permits passage of fluids within the through lumen.

In some embodiments, the gateway element comprises a shape memory material. In some embodiments, the shape memory material comprises nitinol. In some embodiments, the port is configured to be detachable from the conduit. In some embodiments, the conduit comprises a plurality of fluid pathways. In some embodiments, the gateway element comprises a cylindrical portion. In some embodiments, the diameter of the second radially expanded configuration is at least about 50% greater than the first compressed configuration. In some embodiments, the diameter of the second radially expanded configuration is at least about 100% greater than the first compressed configuration. In some embodiments, a diameter of the conduit is between about 4 mm and about 6 mm. In some embodiments, a total axial length of the conduit is between about 3 cm and about 9 cm. In some embodiments, the port is configured to be at least partially subcutaneously implanted. In some embodiments, the port comprises a removable cap configured to reside above the skin surface. In some embodiments, the system can include a plurality of conduits, each conduit comprising a plurality of one-way valves.

In some embodiments, a method of providing access to a target blood vessel is provided. The method can include implanting a port subcutaneously or above the skin and outside of a target blood vessel. The method can include positioning a conduit such that a proximal end of the conduit is fluidly connected to the port and a distal end of the conduit is positioned within the target blood vessel. In some embodiments, the conduit comprises at least one one-way valve within the conduit and proximate the distal end of the conduit. The method can include expanding a gateway element connected proximate the distal end of the conduit such that a first component of the gateway element is positioned outside a sidewall of the target blood vessel. In some embodiments, a second component of the gateway element is positioned inside the sidewall of the target blood vessel. The method can include less than about 5 mm of the distal end of the conduit is positioned within the target blood vessel. In some embodiments, the gateway element comprises a shape memory material.

In some embodiments, a method of providing access to a target blood vessel is provided. The method can include radially expanding a gateway element extending within a subcutaneous tract of a patient. In some embodiments, the gateway element comprises a distal end positioned within a target blood vessel. The method can include accessing a port outside of the target blood vessel. The method can include advancing a medical device through the port, into a conduit within the gateway element, through at least one-way valve, and into the target blood vessel. In some embodiments, the gateway element comprises a shape memory material. In some embodiments, a first component of the gateway element is positioned outside a sidewall of the target blood vessel, a second component of the gateway element is positioned inside the sidewall of the target blood vessel.

In some embodiments, the method can include withdrawing fluid from the target blood vessel through the medical device. In some embodiments, the method can include infusing a therapeutic agent from the target blood vessel through the medical device. In some embodiments, the method can include performing hemodialysis via the medical device. In some embodiments, the target blood vessel comprises a vein. In some embodiments, the method can include a plurality of conduits, each conduit comprising a plurality of one-way valves. In some embodiments, radially expanding the gateway element comprises passively radially expanding the gateway element. In some embodiments, radially expanding the gateway element comprises actively radially expanding the gateway element. In some embodiments, actively radially expanding the gateway element comprises actuating a control to radially expand the gateway element. In some embodiments, the method can include radially contracting the gateway element to minimize dead space and promote occlusion within the gateway element. In some embodiments, radially contracting the gateway element occurs following withdrawing the medical device from the patient. In some embodiments, the gateway element is normally biased in the first, radially compressed configuration. In some embodiments, only a distal segment of the gateway element is normally biased in the first, radially compressed configuration. In some embodiments, the distal segment is configured to be an intravascular segment.

In some embodiments, a luminal access system is provided comprising any one or more of the embodiments described in the disclosure. In some embodiments, a luminal access method is provided comprising any one or more of the embodiments described in the disclosure.

DETAILED DESCRIPTION

Figure 1A:
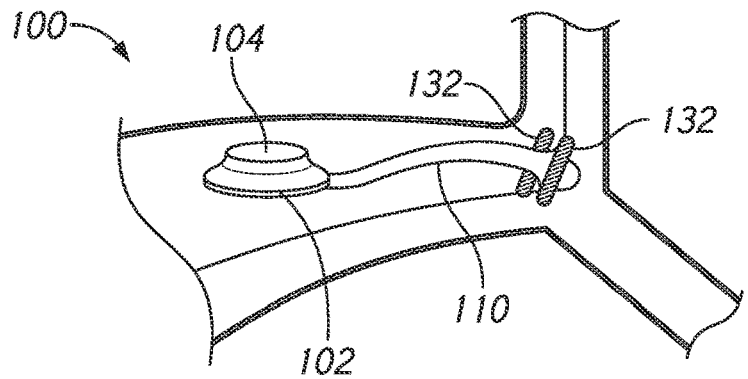
FIGS. 1A-1D schematically illustrates an embodiment of a luminal access system.
Figure 1B:
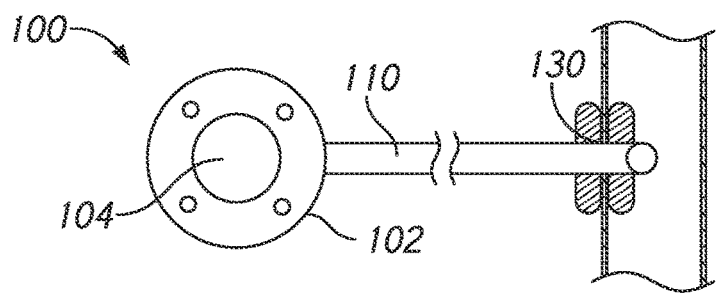
Figure 1C:
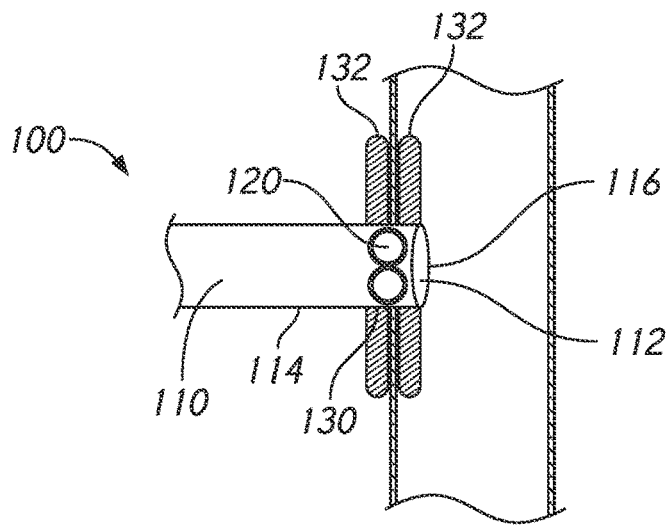
Figure 1D:
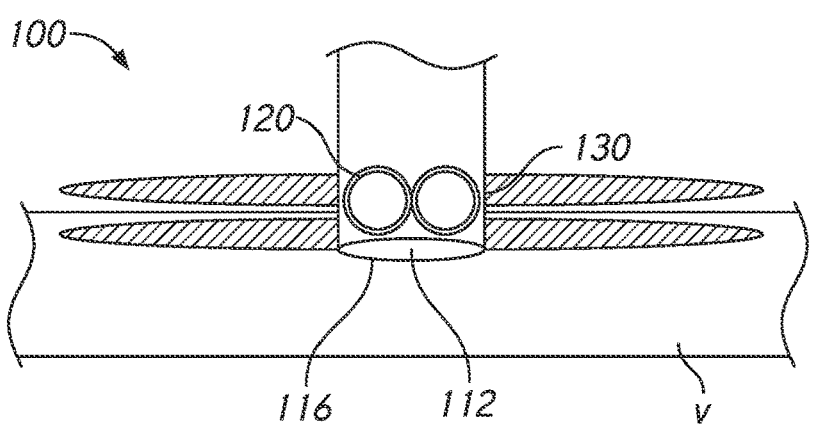

Some embodiments of the invention are configured to accomplish long term dialysis access with the use of ports or gateways into the vascular system that do not comprise indwelling catheters. Some embodiments can advantageously eliminate central venous scarring and subsequent stenoses or occlusions. The risk of infection can also be mitigated due to the lack of an indwelling catheter within the vascular system. Currently, there are no commercially available devices that offer percutaneous long term dialysis access in this method without an indwelling catheter. Conventional surgically placed fistulae and grafts are sewn on to arteries and veins and subsequently do not have indwelling catheters within the system. However, one issue with these fistulae and grafts is that they thrombose quite often, thus requiring "declotting" or thrombectomy interventions. Another issue with these is that they develop other complications, such as outflow vein stenoses, pseudoaneurysms, and even infections. All of these place an enormous burden on the healthcare system for urgent or emergent repair. Some embodiments of the invention can eliminate this by employing one or more valves that seal the device from blood flow when the device is not in use for vascular access, such as dialysis. Additionally, if the device does get infected, which is much less likely than conventional catheters, the subsequent reaction can be much more tolerable than an indwelling infected line, which leads to a more robust immune response, sepsis, and possibly death.

Some embodiments can be utilized in inpatient and outpatient facilities, including hospitals, ambulatory surgical centers, and outpatient dialysis centers. The devices can be utilized by nephrologists and vascular specialists including vascular surgeons and interventional radiologists, and advantageously improve patient satisfaction, cost containment, and improved outcomes.

In some embodiments, a system includes a vascular and/or luminal access device with a low profile intravascular/intraluminal device. The vascular and/or luminal access device can have a low profile state or resting state. The vascular and/or luminal access device can expand to a desired diameter for use. The vascular and/or luminal access device can have an expanded or active state. In some embodiments, the access has an intraluminal component contiguous with or attached to the extraluminal/subcutaneous component.

In some embodiments, intra-vascular elements/components may be catheter tubing or flexible shape memory material, metallic, plastic, or other blended materials such as nitinol and/or silicone. The intra-vascular elements/components can act as a gateway element including a lumen or guide (lumen-guide) for catheters to pass through. The gateway element or lumen-guide can act as a conduit for one or more conduits or other medical devices to pass though it to a desired point in the vessel or body lumen. The material of the lumen-guide is expandable, hence in resting state (lumen-guide without a catheter going through it) it has a fraction of the diameter of the active state (lumen-guide with one or more devices passing through it).

Some embodiments can include three main features, although more or less features can be included in certain systems and methods.

FIGS. 1A-1D schematically illustrates an embodiment of a luminal access system 100. The luminal access system 100 can have any features of any system described herein. The luminal access system 100 can include a port 102. The port 102 can be an external port. The port 102 can be under the skin of the patient. The port 102 can be an internal port. The port 102 can be above the skin of the patient. The port 102 can have a normally open state. The port 102 can have a normally closed state. In the illustrated embodiment, the port 102 is below the skin of the patient. The port 102 can include a lumen 104.

The port 102 can be positioned near the treatment site. The port 102 can be positioned near the vein to be treated. The port 102 can be positioned near the artery to be treated. The port 102 can be at or near the treatment site. The port can be within a distance of the treatment site, wherein the distance is 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, between 1 cm and 10 cm, between 3 cm and 9 cm, between 1 cm and 5 cm, between 5 cm and 12 cm, or any range of two of the foregoing values.

The luminal access system 100 can include a conduit 110. The conduit 110 can be catheter tubing. The conduit 110 can be flexible shape memory material. The conduit 110 can comprise metal, plastic, or other blended materials such as nitinol and/or silicone. The conduit 110 can include a lumen 112. The conduit 110 can connect directly or indirectly to the port 102. The conduit 104 can have a short length. The conduit 110 can have a length of 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, between 1 cm and 10 cm, between 3 cm and 9 cm, between 1 cm and 5 cm, between 5 cm and 12 cm, or any range of two of the foregoing values. The conduit 110 can have a diameter of 1 mm, 2 mm, 3 mm, 4 mm, 5 mm, 6 mm, 7 mm, 8 mm, 9 mm, 10 mm, 11 mm, 12 mm, 13 mcm, 14 mm, 15 mm, 16 mm, 17 mm, 18 mm, 19 mm, 20 mm, between 1 mm and 10 mm, between 4 mm and 6 mm, between 3 mm and 7 mm, or any range of two of the foregoing values. The conduit 110 can span the length between the port 102 and the treatment site. The conduit 110 can include a sidewall 114.

The luminal access system 100 can include a one-way valve 120. The one-way valve 120 can be at the distal of the conduit 110. The one-way valve 120 can be proximate the distal of the conduit 110. The one-way valve 120 can be along the length of the conduit 110. The one-way valve 120 can allow the flow of material in one direction but prevent the flow of material in another direction. The one-way valve 120 can allow passage in one direction but prevent passage in another direction. The one-way valve 120 can allow material to flow into the treatment site, but not out of the treatment site.

The luminal access system 100 can include a gateway element 130. The gateway element 130 can be an expandable shape memory fixture. The gateway element 130 can be cylindrical. The gateway element 130 can any other shape. The gateway element 130 can be coupled to an end of the conduit 110. The gateway element 130 can include one or more anchoring elements 132. The gateway element 130 can include a pair of anchoring elements 132. The anchoring elements 132 can sandwich the vessel wall from both sides in order to secure the conduit 110 in place. The anchoring elements 132 can be positioned on opposite sides of the vessel wall. The vessel wall can be disposed between the anchoring elements 132.

The gateway element 130 can be attached to or otherwise associated with the outer diameter of the one or more conduits 110. The gateway element 130 can house a length of the conduits 110 in a lumen of the gateway element 130 therethrough. In some embodiments, the gateway element 130 can include one or more of an intravascular component and an extravascular component. The anchoring elements 132 can be positioned on either side of the vessel. The anchoring elements 132 are configured to fix the conduit 110 in place to the blood vessel wall by "sandwiching" the blood vessel wall.

The gateway element 130 can take any desired geometry sufficient to fixate the catheter to the blood vessel wall. In some embodiments, the gateway element 130 can take the form of a plurality of movable arms, hooks, or barbs. In some embodiments, the gateway element 130 can take the form of a plurality of movable arms, hooks, or barbs that can extend substantially orthogonal to, or at other angles with respect to the longitudinal axis of the conduit 110. The gateway element 130 can be penetrating or non-penetrating with respect to the target vessel wall.

The conduit 110 can include a tip 116. The tip 116 of the conduit 110 can extend slightly into the vessel, vein, artery, or other treatment site. The tip 116 of the conduit 110 can extend such as about 0.1 mm, 0.2 mm, 0.3 mm, 0.4 mm, 0.5 mm, 1 mm, 2 mm, 3 mm, 4 mm, 5 mm, or any range of two of the foregoing values, or other dimensions as described herein. The luminal access system 100 can include the port 102, the conduit 110, the one-way valve 120 at or proximate the distal end of the conduit, and a shape memory fixture or gateway element 130 that can be cylindrical or other shapes, and sandwiches the vessel wall from both sides in order to secure the catheter in place.

Some embodiments can include an implantable port 102 or other gateway underneath the skin that can have a domed, bubble, or other geometry that can be easily palpable for access by a health care professional, such as dialysis nurses for example. The port 102 or gateway can be made, for example, of a synthetic polymer that is durable and resistant to multiple needle sticks and can be replaced with a minor surgical procedure as needed, such as, e.g., every 5-10 years. In some embodiments, the port 102 can be made of a self-sealing material such as silicone. The port 102 can be free-floating. The port 102 can be sutured or otherwise anchored under the skin. In some embodiments, the port 102 can be a removable port positioned outside of the skin/body, such as a removable mushroom cap-shaped port. The port 102 can be a removable port with a locking feature, such as screw threads or a snap feature, for example.

Another feature of certain systems and methods include one, two, or more conduits 110. Another feature of certain systems and methods include one, two, or more valves 120 per conduit 110. The first valve 120 can be present, for example, at the luminal, e.g., vascular entry point configured so as not to allow blood flow when the device is not in use. The valve 120 can be present near or at the distal end of the conduit 110, and proximate the luminal entry point or the tip 116. The valve 120 could be of a variety of types, including but not limited to pinch, sliding, duckbill, or miter valves. A second valve 120 can be present, for example, at or near the proximal end of the conduit 110, either outside the body or subcutaneous when the system is implanted. The conduit 110 can comprise a single fluid flow path. The conduit 110 can comprise a plurality (e.g., 2, 3, or more) of fluid flow paths (e.g., multiple conduits). The conduit 110 can include coaxial fluid flow paths. The conduit 110 can include non-coaxial fluid flow paths. For example, a first conduit 110, e.g., fluid flow path can be configured for inflow into a lumen of the body, and a second conduit 110, e.g., fluid flow path can be configured for outflow out of a lumen of the body (e.g., for hemodialysis applications). In some embodiments, each fluid flow path can comprise the same diameter. In some embodiments, one fluid flow path can have a larger diameter than another fluid flow path. In some embodiments, each conduit 110 can each comprise proximal and/or distal valves 120. For example, an embodiment with two conduits 110 can include two valves 120 for each conduit for a total of four valves 120. The conduits 110 can include luer lock or other mechanisms associated with the proximal end/valves.

Figure 2A:
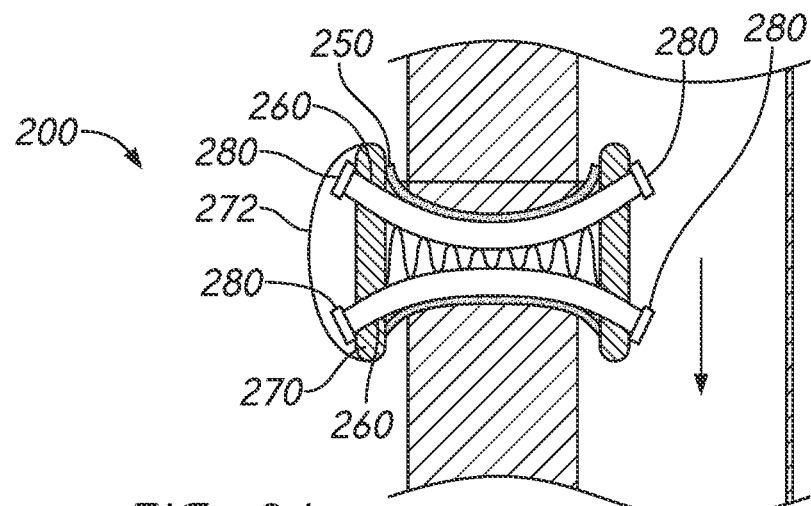
FIGS. 2A-2C schematically illustrates an embodiment of a luminal access system.
Figure 2B:
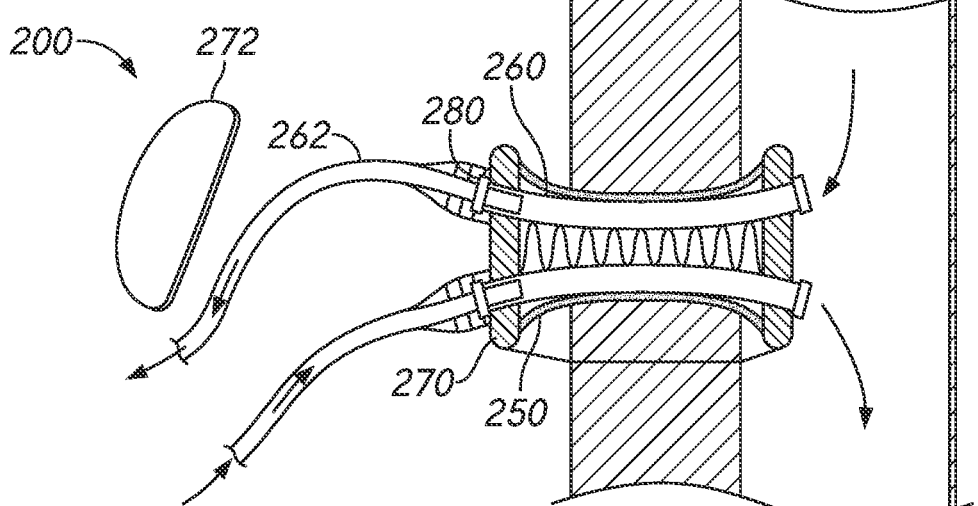
Figure 2C:
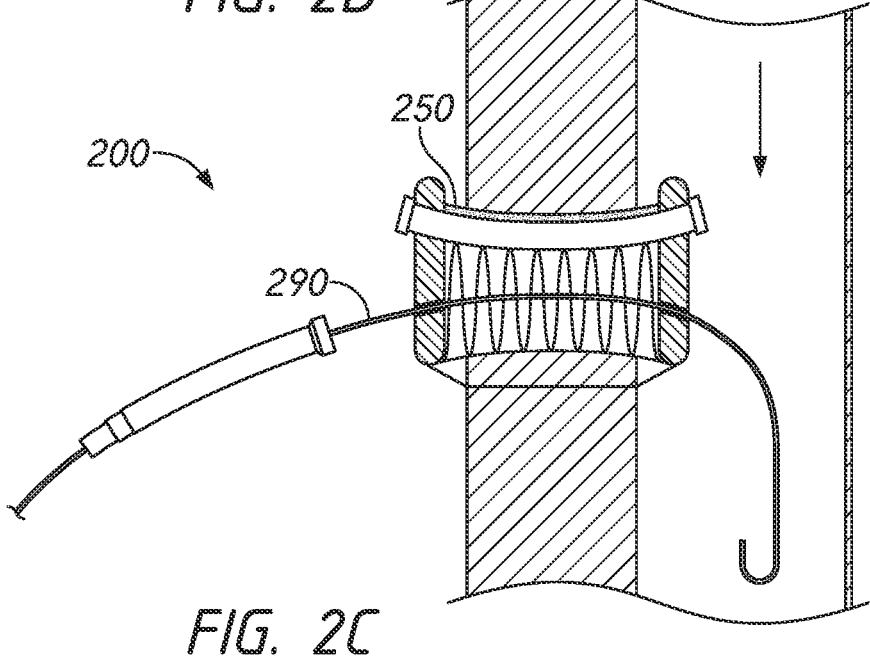

FIGS. 2A-2C schematically illustrates an embodiment of a luminal access system 200. The luminal access system 200 can have any features of any system described herein. The luminal access system 200 can include an expandable and/or contractible gateway element 250. The gateway element 250 can be, for example, a shape memory element. The gateway element 250 can be a nitinol fixture at the vascular entry site. The gateway element 250 can be designed in order to secure a conduit 260 to the blood vessel without the need for an open surgical anastomosis. The gateway element 250 can be configured to expand and contract. The gateway element 250 can be configured to radially expand and contract. The gateway element 250 can be configured to radially expand and contract about a midpoint or centerline. The gateway element 250 can be configured to radially expand and contract about an offset axis. The gateway element 250 can include a lumen 252.

The gateway element 250 can comprises a shape memory material. The term "shape memory material" is used herein to refer to materials which recover from a deformed shape to a pre-formed shape. The shape memory material can be, for example, a shape memory alloy, a shape memory steel alloy or shape memory polymer. In some embodiments, the shape memory material can be Nitinol. In other embodiments, the shape memory material can be a shape memory polymer. Shape-memory polymers can include, e.g. polyurethanes, polyethylene terephthalate (PET), polyethylene oxides (PEO) or block copolymers containing a silicone segment. The gateway element 250 can have a length of 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, between 1 cm and 10 cm, between 3 cm and 9 cm, between 1 cm and 5 cm, between 5 cm and 12 cm, or any range of two of the foregoing values. The gateway element 250 can have a diameter of 1 mm, 2 mm, 3 mm, 4 mm, 5 mm, 6 mm, 7 mm, 8 mm, 9 mm, 10 mm, 11 mm, 12 mm, 13 mcm, 14 mm, 15 mm, 16 mm, 17 mm, 18 mm, 19 mm, 20 mm, between 1 mm and 10 mm, between 4 mm and 6 mm, between 3 mm and 7 mm, or any range of two of the foregoing values.

The gateway element 250 can be attached to one or more conduits 260. The gateway element 250 can be otherwise associated with one or more conduits 260. The gateway element 250 can receive the outer diameter of the one or more conduits 260. and The gateway element 250 can house a length of the conduits 260 in the lumen 252 of the gateway element 250 therethrough. The gateway element 250 can be a shape memory fixture. In some embodiments, the gateway element 250 can include one or more of an intravascular component and an extravascular component. The gateway element 250 can include an intravascular component. The gateway element 250 can include an extravascular component.

The luminal access system 200 can include anchors or anchoring structures configured to fix the conduits 260 in place to the blood vessel wall by "sandwiching" the tissue, a vessel, and/or a subcutaneous tract. The luminal access system 200 can include any anchoring element as described herein. In some embodiments, the gateway element 250 can take the form of a generally tubular, such as a cylindrical shape. In some embodiments, the gateway element 250 can take the form of an hourglass-like shape with larger end diameters and a smaller diameter more centrally. The gateway element 250 can take any desired geometry sufficient to fixate the catheter to the tissue, the blood vessel wall, and/or a subcutaneous tract. In some embodiments, the gateway element 250 can take the form of aa plurality of movable arms, hooks, or barbs. In some embodiments, the gateway element 250 can take the form of a plurality of movable arms, hooks, or barbs that can extend substantially orthogonal to, or at other angles with respect to the longitudinal axis of the conduit 260 and/or gateway element 250. The gateway element 250 can be penetrating or non-penetrating with respect to the tissue, target vessel wall, and/or the subcutaneous tract.

In some embodiments, the conduit 260 can also comprise a shape memory material.

In some embodiments, the gateway element 250 can be configured to be radially expanded actively or passively. The gateway element 250 could be radially expanded passively by introduction of larger catheters/sheaths/devices within the lumen 252 of the gateway element 250. The gateway element 250 can be radially expanded passively by introduction of larger catheters/sheaths/devices within the conduits 260. The gateway element 250 can be radially expanded via an external control element/knob incorporated into a hub of the proximal port 270. The gateway element 250 can be radially expanded by a mechanical expansion mechanism. The gateway element 250 can be radially expanded by an inflatable balloon configured to exert a force on a sidewall of the gateway element 250, and the like. The gateway element 250 can be radially expanded to allow for flow into and/or out of the conduits 260 within the gateway element 250. The gateway element 250 can be radially expanded to allow other medical devices to pass through the gateway element 250 into the target vessel. When use is complete, in some embodiments, the other medical device or other expander can be removed and the gateway element 250 can contract to its unstressed smaller-diameter configuration. When use is complete, in some embodiments, the control element can be actuated to effect transformation of the gateway element 250 to the smaller diameter configuration. The gateway element 250 can have a normally closed or contracted state. The gateway element 250 can have a closed shape memory state. The gateway element 250 can prevent the flow of material when closed. The gateway element 250 can be actively expanded. The gateway element 250 can be passively expanded. The gateway element 250 can be expanded by insertion of the conduits 260, a mechanical expander, or other medical tools. The gateway element 250 can be contracted by removal of the conduits 260, a mechanical expander, or other medical tools. The gateway element 250 can be expanded by insertion of tools or other devices through the lumen 252 of the gateway element 250. The gateway element 250 can be contracted by removal of tools or other devices through the lumen 252 of the gateway element 250.

In some embodiments, the blood vessel accessed is a vein or an artery. The vein could be, in some cases, an internal jugular vein, external jugular vein, superior vena cava, subclavian vein, brachiocephalic vein, axially vein, basilic vein, cephalic vein, brachial vein, inferior vena cava, iliac vein, or femoral vein. In some embodiments, the system can be positioned within a chamber of the heart, such as the right atrium, for example. In some embodiments, the system can be positioned near the treatment site. The system can be positioned to reduce the length the gateway element 250.

In some embodiments, only a very short segment of length of the distal end of the conduit(s) 260 and/or the gateway element 250, such as the distal tip, resides within the target lumen long-term. The length of conduit 260 actually within the target lumen when implanted can be, for example, less than about 10 mm, 9 mm, 8 mm, 7 mm, 6 mm, 5 mm, 4 mm, 3 mm, 2 mm, 1 mm, or less, or ranges including any two of the foregoing values. The length of conduit 260 actually within the target lumen when implanted can be, for examples, less than about 15%, 10%, 9%, 8%, 7%, 6%, 5%, 4%, 3%, 2%, 1%, or even less of the total axial length of the catheter, or ranges including any two of the foregoing values. The length of gateway element 250 actually within the target lumen when implanted can be, for example, less than about 10 mm, 9 mm, 8 mm, 7 mm, 6 mm, 5 mm, 4 mm, 3 mm, 2 mm, 1 mm, or less, or ranges including any two of the foregoing values. The length of gateway element 250 actually within the target lumen when implanted can be, for examples, less than about 15%, 10%, 9%, 8%, 7%, 6%, 5%, 4%, 3%, 2%, 1%, or even less of the total axial length of the catheter, or ranges including any two of the foregoing values.

In some embodiments, only the shape memory component of the gateway element 250 resides in the target lumen when not being used. In some embodiments, a shorter axial segment of conduit 260 resides in the target lumen when not being used (compared with the shape memory element).

In some embodiments, the total axial length of the conduit(s) 260 and/or the gateway element 250 can be, for example, about, at least about, or no more than about 2 cm, 3 cm, 4 cm, 5 cm, 6 cm, 7 cm, 8 cm, 9 cm, 10 cm, 11 cm, 12 cm, or ranges including any two of the foregoing values.

In some embodiments, the diameter of the conduit 260 and/or the gateway element 250 (in either an expanded or reduced configuration) can be, for example, about, at least about, or no more than about 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 35 mm, or more or less, or ranges including any two of the foregoing values. In some embodiments, the gateway element 250 can radially expand (or contract) by, for example, about, at least about, or no more than about 10%, 20%, 30%, 40%, 50%, 60%, 70%, 80%, 90%, 100%, 125%, 150%, 175%, 200%, or more or less, or ranges including any two of the foregoing values. In some embodiments, the gateway element 250 has a diameter that is about, or less than about 50%, 40%, 30%, 20%, 10%, 5%, 4%, 3%, 2%, 1%, or less of the diameter of the target vessel in its radially reduced and/or unstressed state, such that it has a minimal footprint in the target vessel when not being used.

In some embodiments, the gateway element 250 and/or the conduit 260 can comprise one, two, or more therapeutic agents, such as drugs (e.g., coated to the distal end of the conduit). The drug could include, for example, an antithrombotic agent such as heparin, warfarin, fragmin, danadparoid, enoxaparin, tinzaparin, or fondaparinux. In some embodiments, the drug could include an antibiotic agent. In some embodiments, a diagnostic and/or therapeutic medical device can be attached or otherwise associated with the gateway element, such as a sensor and/or a drug delivery element, for example.

FIG. 2A schematically illustrates an embodiment of the luminal access system 200 post-implantation. Illustrated are a proximal port 270. The proximal port 270t can include a removable cap 272. The luminal access system 200 can include a plurality of conduits 260, each with valves 280 near each conduit's proximal end and distal end. The valve 280 can be a one-way valve. Each conduit 260 can have one or more valves 280. The gateway element 250 can be a shape memory conduit. The proximal port 270 can be outside of the patient as shown, or partially or entirely subcutaneous in other embodiments. The cap 272 can be removable. The cap 272 can be a re-sealable barrier in other embodiments, such as subcutaneous embodiments, and accessed with aseptic techniques to ensure sterility. The gateway element 250 can span a subcutaneous tract between the skin surface (or above the skin surface) and the target lumen (e.g., a vascular lumen, such as a vein). The vein is also shown. The direction of blood flow can be downward as shown by the arrow. The conduits 260 can be cannulas that direct the flow of materials or tools. The top conduit 260 can be an arterial cannula. The bottom conduit 260 can be a venous cannula. The conduit 260 can have one or more valve 280. The gateway element 250 can be a nitinol conduit. The luminal access system 200 can include one or more luer locks. The proximal port can include one or more luer locks. The proximal port 270 can be a removable port mushroom cap 272. The proximal port can screw on and off. The skin of the patient is also shown. The gateway element 250 spans the subcutaneous tract.

FIG. 2B schematically illustrates the luminal access system in use for hemodialysis, dialysis or other infusion. The cap 272 is removed. The luer lock through the proximal valves 280 breaks lock and creates a flow channel. The cap can be screwed on and off with a technique to maintain sterility. The conduits 260 are connected to luer lock tubing 262. The conduit 260 are attached to tubing 262 through the proximal valves 280. The top conduit 260 can be to dialysate, and the bottom conduit can be from dialysate. The arrows show the direction of flow. The luminal access system 200 can include the first conduit 260 for outflow (e.g., to dialysate), and the second conduit 260 for inflow (e.g., to dialysate), with luer lock or other tubing serving as the conduits. The gateway element 250 can be radially expanded passively or actively as noted above to allow flow to and/from the target vessel. The gateway element 250 can be radially contracted following use to occlude the subcutaneous tract. In some embodiments, the gateway element 250 can self-expand. In some embodiments, the gateway element 250 can self-contract.

FIG. 2C schematically illustrates replacement of a malfunctioning or aged conduit 260, while maintaining the gateway element 250 in place. This can also be utilized to introduce other medical devices or for urgent vascular access without necessarily replacing a conduit 260. The gateway element 250 can be expanded as noted above. A guidewire 290 can be used to replace the conduit 260. The guidewire 290 can be threaded through the target conduit 260 into the target vessel, the conduit 260 removed, a new conduit 260 (including one or more valves 280 as noted above) inserted over the guidewire 290 into the gateway element 250, the guidewire 290 can be withdrawn, and the gateway element 250 can be transformed back to the radially reduced configuration to occlude the subcutaneous tract. The conduit 260 can have over the wire removal. The new conduit 260 can be introduced over the guide wire 290. The gateway element 250 shifts to pack the dead space and becomes occlusive.

In some embodiments, a luminal access system 200 may include a single, or a plurality of conduits 260 that can be used for therapeutic infusions (e.g., chemotherapy or other long-term infusion) and/or blood draws.

Figure 3A:
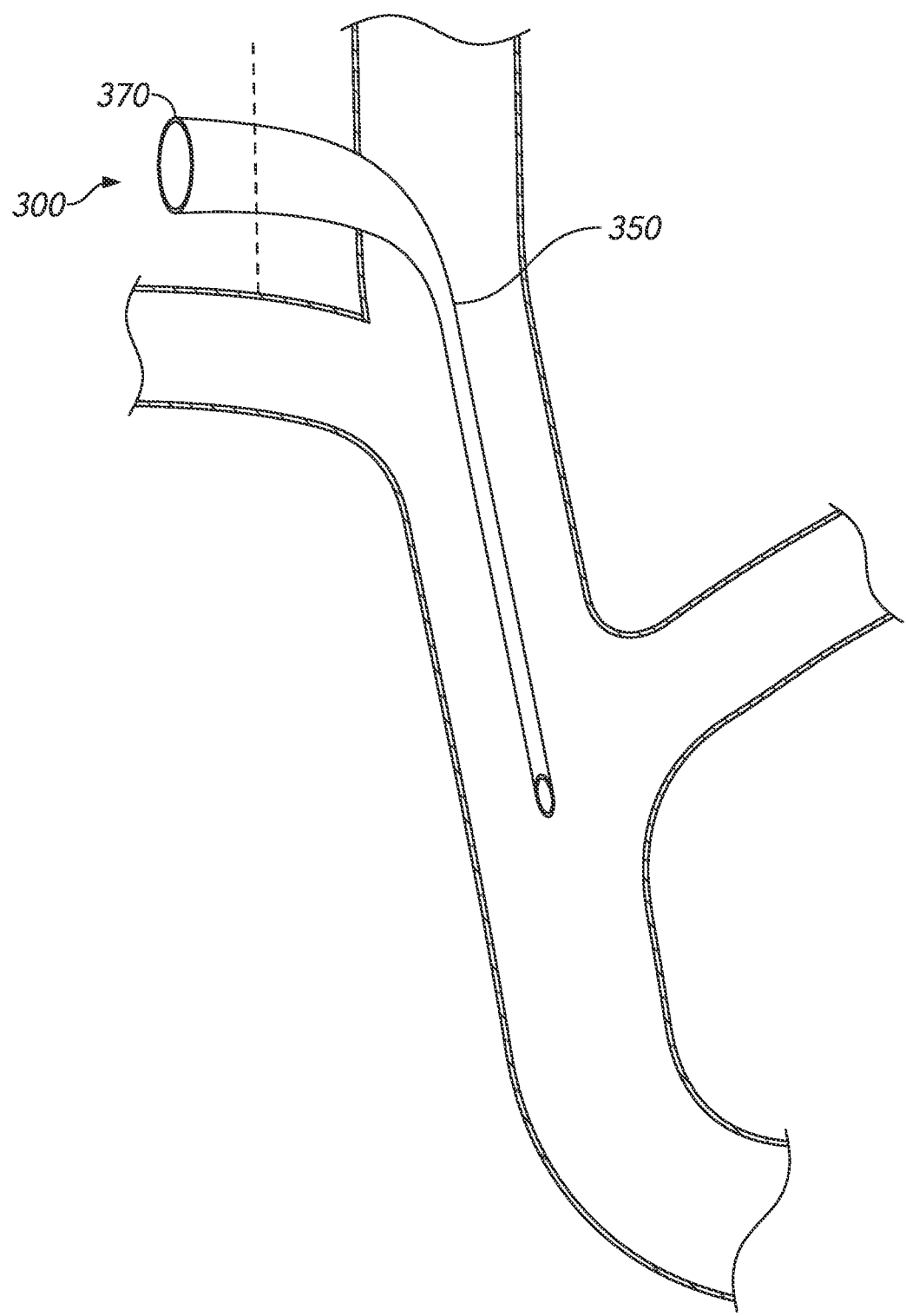
FIGS. 3A-3D further illustrate additional embodiments and/or features of a luminal access system.

FIG. 3A schematically illustrates another embodiment of a luminal access system 300. The luminal access system 300 can have any features of any system described herein. The luminal access system 300 can include a gateway element 350. The luminal access system 300 can include a single port 370. The luminal access system 300 can include a plurality of cutaneous and/or subcutaneous ports 370. The port 370 can be locate at a proximal end of the gateway element 350. The gateway element 350 can serve as a conduit itself. The gateway element 350 can include one, two, three, or more discrete conduits within a lumen 352 of the gateway element 350. At least part of the gateway element 352 (e.g., at least, or only, an intravascular segment) can include a radially contracted configuration as shown, which can passively or actively radially expand as previously described. In some embodiments, only about, at least about, or no more than about the distal-most 10 cm, 9 cm, 8 cm, 7 cm, 6 cm, 5 cm, 4 cm, 3 cm, 2 cm, 1 cm, or more or less (or ranges including any two of the foregoing values) of the gateway element 350 is subject to radial change or expansion by about or at least about 5%, 10%, 15%, 20%, 25%, 30%, 35%, 40%, 45%, 50%, 60%, 70%, 80%, 90%, 100%, 125%, 150%, 175%, 200%, or more or less (or ranges including any two of the foregoing values). In some embodiments, a portion of the gateway element 350 is not subject to radial change or expansion. The gateway element 350 can serve as a vascular window. The luminal access system 300 can include an external component, hub, or port 370. The gateway element 350 can be an expandable, intraluminal component. The gateway element 350 can be made of shape memory material. The gateway element 350 can be coated with non-thrombogenic material. The gateway element 350 can be coated with a polymer or silicon. The gateway element 350 can be expanded by insertion of a device through it. The gateway element 350 can be expanded by actuating the expanding mechanism at the external hub or port 370. The gateway element 350 can have a length of 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, between 1 cm and 10 cm, between 3 cm and 9 cm, between 1 cm and 5 cm, between 5 cm and 12 cm, or any range of two of the foregoing values. The gateway element 350 can have a diameter of 1 mm, 2 mm, 3 mm, 4 mm, 5 mm, 6 mm, 7 mm, 8 mm, 9 mm, 10 mm, 11 mm, 12 mm, 13 mcm, 14 mm, 15 mm, 16 mm, 17 mm, 18 mm, 19 mm, 20 mm, between 1 mm and 10 mm, between 4 mm and 6 mm, between 3 mm and 7 mm, or any range of two of the foregoing values.

The gateway element 350 can act as a conduit for introduction of devices into the body or vasculature. The gateway element 350 can be radially expanded passively by introduction of larger catheters, sheaths, expander, and/or devices within the lumen 352 of the gateway element 350. The gateway element 350 can be radially expanded via any mechanism described herein. The gateway element 350 can be radially expanded to allow other medical devices to pass through the gateway element 350 into the body or vessel. When use is complete, in some embodiments, the other medical device or other expander can be removed and the gateway element 350 can contract to its unstressed smaller-diameter configuration. The gateway element 350 can have a normally closed or contracted state. The gateway element 350 can be hollow. The gateway element 350 can include the lumen 352 as shown. In other embodiments, the gateway element 350 can be solid. The gateway element 350 can be a wire. The gateway element 350 can be fixated extravascularly. The gateway element 350 can be fixated to subcutaneous tissues. The gateway element 350 can be fixated outside to the skin.

Figure 3B:
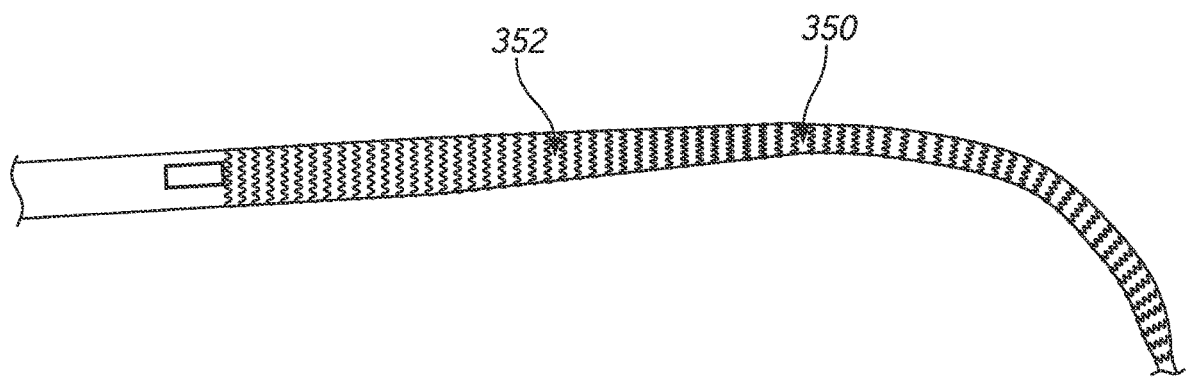

FIG. 3B illustrates an embodiment of the gateway element 350 that includes a shape memory frame overlying at least a portion of the inner lumen 352, which could be a conduit per se as previously described. The gateway element 350 can alternatively house discrete conduits within the inner lumen 352, such as conduits 260. In some embodiments, the inner lumen 352 is defined by the shape memory frame of the gateway element 350 without any separate inner layers of non-shape memory materials. The shape memory frame of the gateway element 350 can include interstices as shown. The inner lumen 352 could be made of non-shape memory materials, including silicone, polymers, plastic, PTFE, ePTFE, and other biocompatible catheter and graft materials, for example. Radial expansion of the shape memory frame of the gateway element 350 can occur passively or actively as previously described, with corresponding expansion of the inner lumen 352. Following removal of a medical device placed within the inner lumen 352 to expand the gateway element 350 and/or actuation of a control element, the shape memory frame of the gateway element 350 can radially contract, in turn radially contracting the inner lumen 352 and decreasing the profile and/or inhibiting flow within the gateway element 350.

In some embodiments, the shape memory frame of the gateway element 350 extends radially outward of, and over an axial length of about, at least about, or no more than about 5%, 10%, 15%, 20%, 25%, 30%, 35%, 40%, 45%, 50%, 55%, 60%, 65%, 70%, 75%, 80%, 85%, 90%, 95%, or 100%, or more or less of the entire gateway element 350, including ranges including any two of the foregoing values.

Figure 3C:
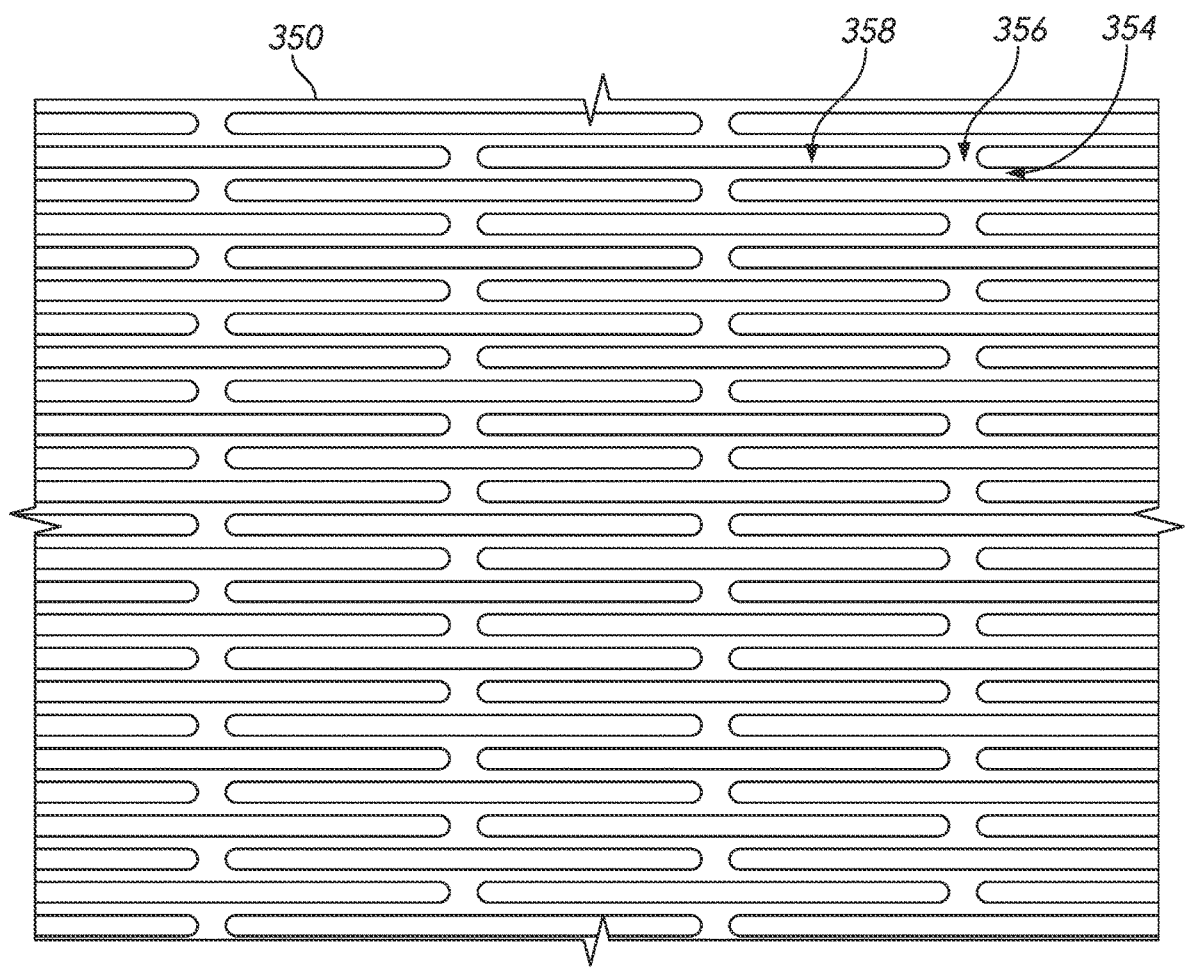
Figure 3D:
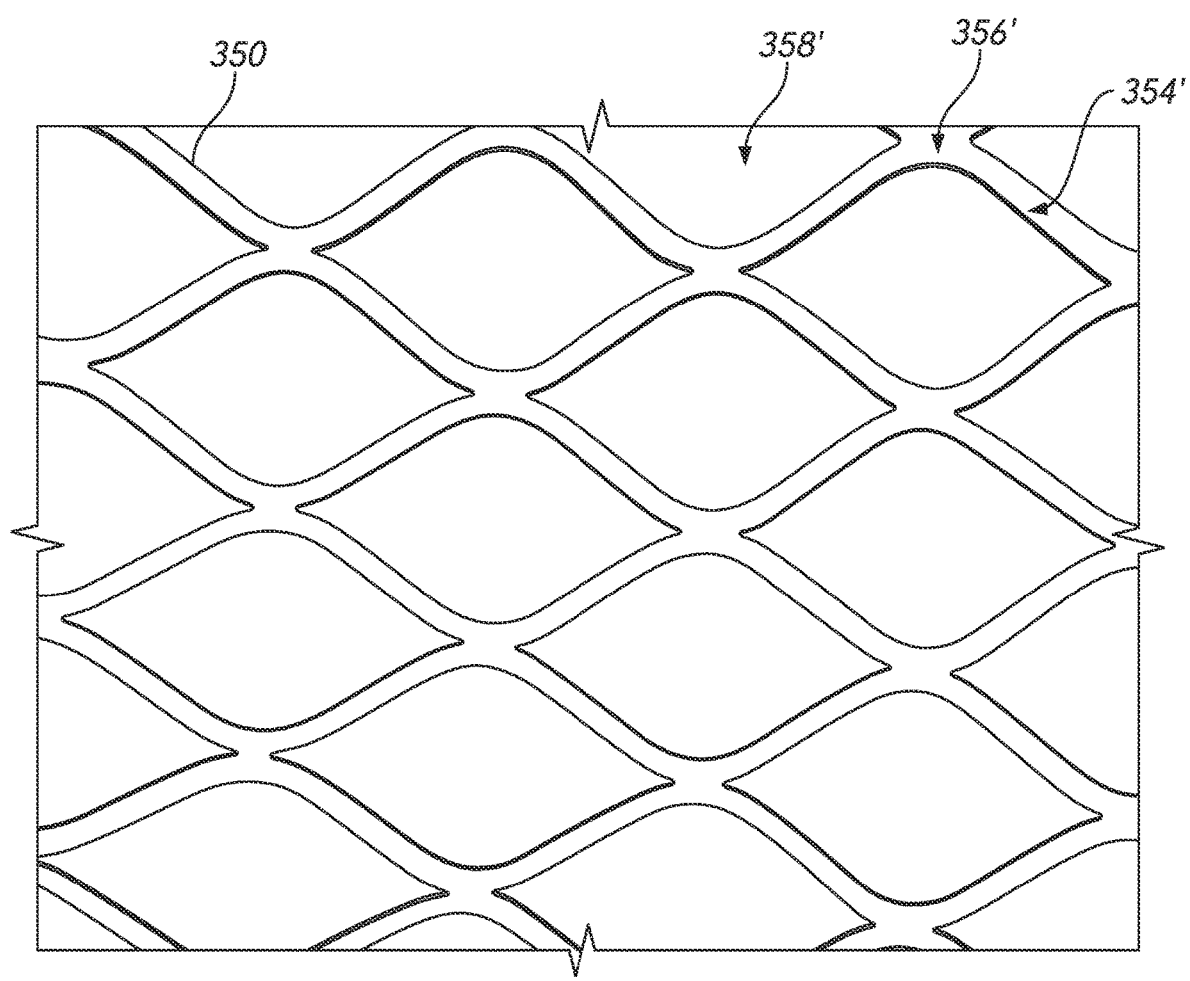

FIG. 3C schematically illustrates a wall pattern of a shape memory frame of the gateway element 350 in an unstressed, radially contracted state, including longitudinal struts 354 interconnected by crossing struts 356 defining interstices 358 therebetween. FIG. 3D schematically illustrates the wall pattern of FIG. 3C in an expanded configuration, illustrating the longitudinal struts 354' taking a sinusoidal pattern, intersecting crossing struts 356' and enlarged interstices 358' therebetween. Various other wall patterns can also be utilized depending on the desired clinical result.

The gateway element 350 can include a shape memory frame that can be coated with, for example, a non-thrombogenic material such as a polymer, silicone, etc. The shape memory frame can overlie and at least partially overlap with an inner lumen as described elsewhere herein.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a needle through a subcutaneous port" includes "instructing the inserting a needle through a subcutaneous port." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A vascular access system, comprising:
   a port configured to be implanted outside of a target body lumen;
   at least one conduit fluidly connected to the port, the conduit comprising an open proximal end, an open distal end, and a sidewall defining a fluid pathway therethrough;
   at least one one-way valve proximate the distal end of the conduit and within the fluid pathway of the sidewall of the conduit; and
   a gateway element comprising a through lumen operably connected to an outer diameter of the conduit, the gateway element comprising a first radially compressed configuration in which the gateway element causes occlusion within the through lumen, and a second radially expanded configuration in which the gateway element permits passage of fluids within the through lumen.

2. The system of claim 1, wherein the gateway element comprises a shape memory material.

3. The system of claim 2, wherein the shape memory material comprises nitinol.

4. The system of claim 1, wherein the port is configured to be detachable from the conduit.

5. The system of claim 1, wherein the conduit comprises a plurality of fluid pathways.

6. The system of claim 1, wherein the gateway element comprises a cylindrical portion.

7. The system of claim 1, wherein the diameter of the second radially expanded configuration is at least about 50% greater than the first compressed configuration.

8. The system of claim 1, wherein the diameter of the second radially expanded configuration is at least about 100% greater than the first compressed configuration.

9. The system of claim 1, wherein a diameter of the conduit is between about 4 mm and about 6 mm.

10. The system of claim 1, wherein a total axial length of the conduit is between about 3 cm and about 9 cm.

11. The system of claim 1, wherein the port is configured to be at least partially subcutaneously implanted.

12. The system of claim 1, wherein the port comprises a removable cap configured to reside above the skin surface.

13. The system of claim 1, comprising a plurality of conduits, each conduit comprising a plurality of one-way valves.

14. The system of claim 1, wherein the gateway element is normally biased in the first, radially compressed configuration.

15. The system of claim 14, wherein only a distal segment of the gateway element is normally biased in the first, radially compressed configuration.

16. The system of claim 15, wherein the distal segment is configured to be an intravascular segment.

17. A method of providing access to a target blood vessel, comprising:
    implanting a port subcutaneously or above the skin and outside of a target blood vessel;
    positioning a conduit such that a proximal end of the conduit is fluidly connected to the port and a distal end of the conduit is positioned within the target blood vessel, the conduit comprising at least one one-way valve within the conduit and proximate the distal end of the conduit; and
    expanding a gateway element connected proximate the distal end of the conduit such that a first component of the gateway element is positioned outside a sidewall of the target blood vessel, a second component of the gateway element is positioned inside the sidewall of the target blood vessel, and less than about 5 mm of the distal end of the conduit is positioned within the target blood vessel.

18. The method of claim 17, wherein the gateway element comprises a shape memory material.

19. The method of claim 17, further comprising withdrawing fluid from the target blood vessel through the medical device.

20. The method of claim 17, further comprising infusing a therapeutic agent from the target blood vessel through the medical device.

21. The method of claim 17, further comprising performing hemodialysis via the medical device.

22. The method of claim 17, wherein the target blood vessel comprises a vein.

23. The method of claim 17, comprising a plurality of conduits, each conduit comprising a plurality of one-way valves.

24. A method of providing access to a target blood vessel, comprising:
    radially expanding a gateway element extending within a subcutaneous tract of a patient, the gateway element comprising a distal end positioned within a target blood vessel
    accessing a port outside of the target blood vessel;
    advancing a medical device through the port, into a conduit within the gateway element, through at least one-way valve, and into the target blood vessel,
    wherein the gateway element comprises a shape memory material, and a first component of the gateway element is positioned outside a sidewall of the target blood vessel, a second component of the gateway element is positioned inside the sidewall of the target blood vessel.

25. The method of claim 19, further comprising radially contracting the gateway element to minimize dead space and promote occlusion within the gateway element.

26. The method of claim 25, wherein radially contracting the gateway element occurs following withdrawing the medical device from the patient.

27. The method of claim 24, wherein radially expanding the gateway element comprises passively radially expanding the gateway element.

28. The method of claim 24, wherein radially expanding the gateway element comprises actively radially expanding the gateway element.

29. The method of claim 24, wherein actively radially expanding the gateway element comprises actuating a control to radially expand the gateway element.

* * * * *